US010525281B2

(12) United States Patent
Fukumoto et al.

(10) Patent No.: US 10,525,281 B2
(45) Date of Patent: Jan. 7, 2020

(54) SPACER FOR IONIZED RADIATION THERAPY

(75) Inventors: Takumi Fukumoto, Hyogo (JP); Tsutomu Obata, Hyogo (JP); Yoshitaka Tagami, Hyogo (JP); Eiichi Uemura, Osaka (JP); Michiko Manabe, Osaka (JP)

(73) Assignees: National University Corporation Kobe University, Hyogo (JP); Kanai Juyo Kogyo Co., LTD., Hyogo (JP); Alfresa Pharma Corporation, Osaka (JP)

( * ) Notice: Subject to any disclaimer, the term of this patent is extended or adjusted under 35 U.S.C. 154(b) by 692 days.

(21) Appl. No.: 13/504,989

(22) PCT Filed: Oct. 28, 2010

(86) PCT No.: PCT/JP2010/069124
§ 371 (c)(1),
(2), (4) Date: Jul. 10, 2012

(87) PCT Pub. No.: WO2011/055670
PCT Pub. Date: May 12, 2011

(65) Prior Publication Data
US 2012/0271093 A1 Oct. 25, 2012

(30) Foreign Application Priority Data
Nov. 5, 2009 (JP) .................... 2009-254145

(51) Int. Cl.
*A61N 5/10* (2006.01)
*G21F 3/00* (2006.01)
(Continued)

(52) U.S. Cl.
CPC .................. *A61N 5/10* (2013.01); *G21F 3/00* (2013.01); *A61B 2090/0445* (2016.02);
(Continued)

(58) Field of Classification Search
CPC .... A61N 2005/1094; A61N 2005/1096; A61B 2019/4045; A61B 2090/0445; A61B 2090/0815; A61B 2017/00898
(Continued)

(56) References Cited

U.S. PATENT DOCUMENTS 2,423,707 A * 7/1947 Kenyon et al. ........... 139/426 R
3,961,629 A * 6/1976 Richter ............... A61F 13/2082
604/369

(Continued)

FOREIGN PATENT DOCUMENTS

CN 101301496 A 11/2008
CN 101507843 A 8/2009
(Continued)

OTHER PUBLICATIONS

International Search Report issued in corresponding International Patent Application No. PCT/JP2010/069124 dated Dec. 7, 2010 (2 pages).
(Continued)

*Primary Examiner* — Kaylee R Wilson
(74) *Attorney, Agent, or Firm* — Kilyk & Bowersox, P.L.L.C.

(57) ABSTRACT

Provided is a spacer for ionizing radiation therapy, which can be easily disposed in a living body, does not require abdominal surgery for removing the disposed spacer after radiation therapy, and can effectively separate a tissue to be treated from other tissues. The spacer for ionizing radiation therapy includes a fiber assembly obtained by three-dimensionally entangling a fibrous material formed of a biocompatible synthetic polymeric material. Specifically, the spacer has a thickness of 1 mm to 100 mm.

11 Claims, 3 Drawing Sheets

(51) Int. Cl.
*G21F 1/10* (2006.01)
*A61B 90/00* (2016.01)

(52) U.S. Cl.
CPC ............ *A61B 2090/0815* (2016.02); *A61N 2005/1094* (2013.01); *A61N 2005/1096* (2013.01); *G21F 1/10* (2013.01)

(58) Field of Classification Search
USPC ...................................... 600/3, 201; 604/358
See application file for complete search history.

(56) References Cited

U.S. PATENT DOCUMENTS

| | | | |
|---|---|---|---|
| 4,754,745 | A | 7/1988 | Horowitz |
| 5,648,141 | A * | 7/1997 | Butterworth ............ A61F 13/36 428/131 |
| 7,465,847 | B2 * | 12/2008 | Fabian ......................... 604/362 |
| 7,726,318 | B2 * | 6/2010 | Francescatti ........... A61B 19/40 128/897 |
| 8,343,135 | B2 * | 1/2013 | Porto et al. .................... 604/523 |
| 8,696,539 | B2 * | 4/2014 | Popowski ............ A61N 5/1015 600/3 |
| 2002/0148980 | A1 * | 10/2002 | Cadwalader et al. ..... 250/515.1 |
| 2005/0209574 | A1 * | 9/2005 | Boehringer et al. .......... 604/289 |
| 2006/0189838 | A1 * | 8/2006 | Dejuan et al. .................... 600/3 |
| 2008/0039676 | A1 * | 2/2008 | Fischeii et al. .................. 600/12 |
| 2008/0123810 | A1 * | 5/2008 | Kirkpatrick et al. ........... 378/65 |
| 2009/0075542 | A1 * | 3/2009 | Cuypers .................. A61F 13/04 442/181 |
| 2009/0196901 | A1 * | 8/2009 | Guilak et al. .................. 424/423 |
| 2009/0232920 | A1 * | 9/2009 | Lozano et al. ............... 425/72.2 |

FOREIGN PATENT DOCUMENTS

| | | |
|---|---|---|
| JP | H04-031071 A | 7/1992 |
| JP | 11-253564 | 9/1999 |
| JP | 2005-287728 | 10/2005 |
| JP | 2009-512475 | 3/2009 |
| WO | WO 2006107388 A1 * | 10/2006 |
| WO | 2007045913 A2 | 4/2007 |
| WO | WO 2007109284 A2 * | 9/2007 |

OTHER PUBLICATIONS

MVS-8-11, "Case Study of Spacer Insertion Employed for Heavy Particle Radiotherapy against Hepatic Cancers," The 21st Meeting of Japanese Society of Hepato-Biliary-Pancreatic Surgery, 2009 (in Japanese with English translation attached) (3 pages).

WS-1-4, "Fusion of Particle Beam Therapy and Surgical Therapy: Broadened Application of Particle Beam Therapy by Spacer Operation," Journal of Japan Surgical Society, vol. 110, Supplement (2), p. 155 (in Japanese with English translation attached) (2 pages).

Nakanishi et al., "Positively Charged Liposome Functions as an Efficient Immunoadjuvant in Inducing Immune Responses to Soluble Proteins," Biochemical and Biophysical Research Communications, Article No. RC977749, vol. 240, 1997, pp. 793-797 (5 pages).

Rosenberg et al., "Immunologic and therapeutic evaluation of a synthetic peptide vaccine for the treatment of patients with metastatic melanoma," Nature Medicine, vol. 4(3), Mar. 1998, pp. 321-327 (16 pages).

Golumbek et al., "Controlled Release, Biodegradable Cytokine Depots: A New Approach in Cancer Vaccine Design," Cancer Research, vol. 53, Dec. 15, 1993, pp. 5841-5844 (5 pages).

* cited by examiner

[FIG. 1]
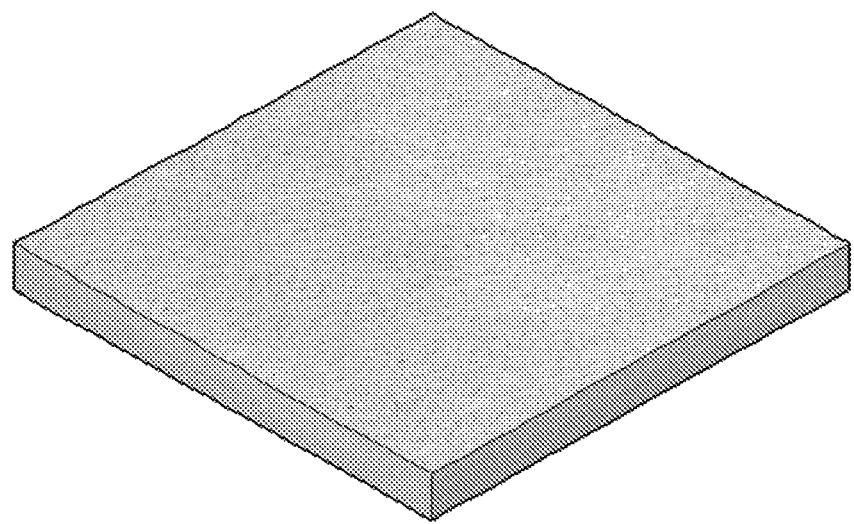

[FIG. 2]
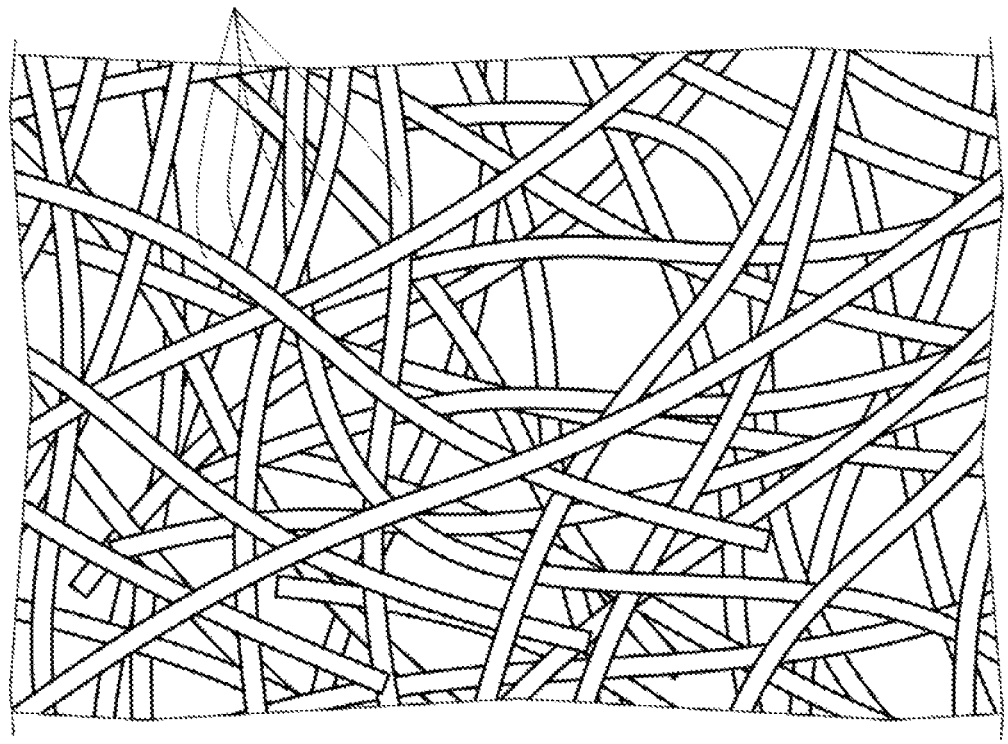

[FIG. 3]
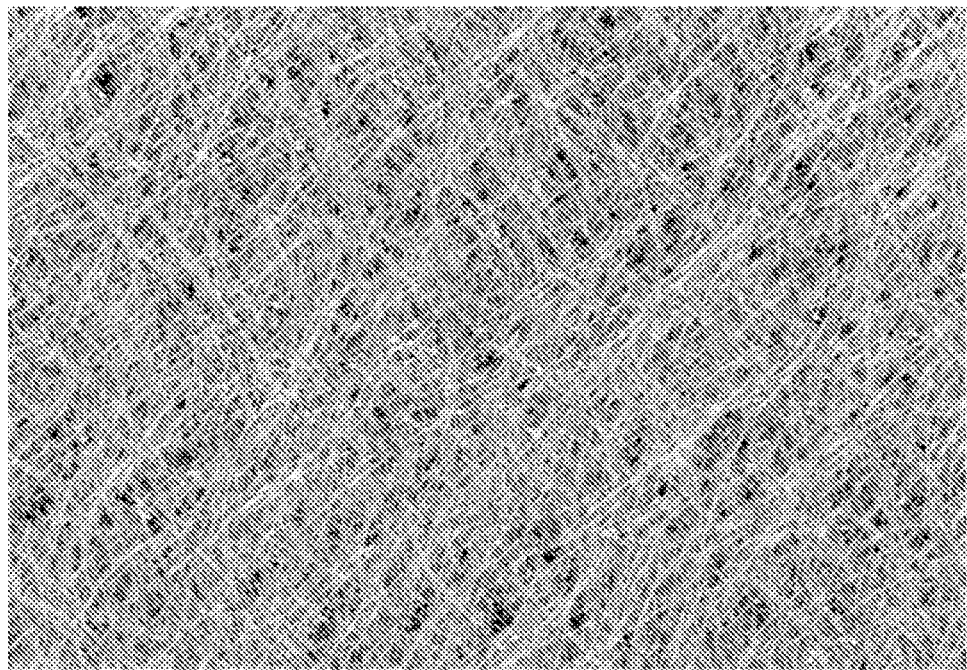

SPACER FOR IONIZED RADIATION THERAPY

TECHNICAL FIELD

The present invention relates to a spacer for ionizing radiation therapy to be used for aiding ionizing radiation therapy.

The present application is a National Stage Application of PCT/JP2010/069124, filed Oct. 28, 2010, which claims priority from Japanese Patent Application No. 2009-254145, which is incorporated herein by reference.

BACKGROUND ART

Ionizing radiation therapy is a therapeutic method involving irradiating a lesion with radiation to kill cells in the lesion. This therapy is used for not only malignant tumors but also some benign diseases, for example, in improving a keloid and treating thyroid ophthalmopathy. The ionizing radiation therapy is one of the major therapeutic methods for malignant tumors, but known to have a problem of an adverse effect of damaging normal organs and tissues surrounding the lesion by exposure. In order to reduce such adverse effect, efforts have been made to avoid exposure of normal tissues. For example, there has been offered a method involving irradiating a lesion from a close distance with a high-energy electron beam that does not reach a deep portion, such as a particle beam, thereby irradiating the lesion with a high dose of radiation at one time without any adverse effect, which is impossible with extracorporeal irradiation. It can be said that a therapeutic method based on the particle beam irradiation is excellent in dose concentration, sharpness of a dose distribution boundary, biological effect (killing effect), effect on a hypoxic cancer, effect on a radioresistant cancer, and the like as compared to X-ray irradiation. However, even in the case of the particle beam irradiation, exposure of any normal tissue should be avoided as much as possible.

As a method of avoiding exposure of a normal tissue, there is given, for example, a method involving, in irradiation of a lesion with radiation, performing highly accurate positioning of a target and three-dimensionally concentrating a high-energy beam on the resultant position with high precision (three-dimensional irradiation method). In addition, there has also been adopted a method of avoiding exposure of a normal tissue involving fixing a site to be irradiated from the outside with, for example, various mechanical fixtures and shells made of plastics to reduce the movement of the target. However, movements of organs include vital ones such as a respiratory motion and a heartbeat, and hence should not be regulated completely.

As means for solving the problems, there has been proposed an artificial material which is disposed between a lesion and an adjacent normal tissue to separate the normal tissue to a position with no risk of exposure (spacer). As such spacer for ionizing radiation therapy (hereinafter, sometimes simply referred to as "spacer"), there has been known an approach of using a medical material produced by combining a film obtained by subjecting polytetrafluoroethylene to stretch processing and a polyurethane polymer, such as a GORE-TEX™ (Non Patent Literatures 1 and 2). The GORE-TEX™ is a medical material and has assured safety for use in a living body. However, the spacer is removed by performing abdominal surgery again after the completion of ionizing radiation therapy in order to eliminate a problem that may arise if foreign matter is left in the body.

However, repeated abdominal surgery involves a burden on and a risk to a patient, and when the spacer and a normal tissue adhere to each other, an adhesiotomy or the like is necessary, resulting in a further increased burden on and risk to the patient. As means for solving this problem, Patent Literature 1 and Patent Literature 2 each propose a spacer that does not need to be removed after therapy. The implant (spacer) disclosed in Patent Literature 1 contains a biocompatible material implantable with a tube, a hose, an injection needle, or the like in a non-open surgical manner, has a viscosity at 37° C. before implantation in the range of 20 to 3,000 mPa·s, and shows an increase in viscosity after implantation as compared to before implantation. As a result of containing the biocompatible material, the spacer does not require abdominal surgery for removing the implant after therapy. In addition, when a biodegradable material is used for the biocompatible material, the implant does not remain in the body because the material is naturally degraded in the living body.

The sponge (spacer) for radiation therapy disclosed in Patent Literature 2 is constructed of collagen having an intermolecular cross-link or a mixture of collagen and gelatin. The sponge has compression recoverability, and hence separation of a normal tissue can be performed by introducing the sponge in a compressed state into the intraperitoneal cavity with a tracker or the like, and recovering the sponge to its original form through utilization of intraperitoneal water or the like. Further, the sponge is insoluble in water at an early stage after its introduction into the intraperitoneal cavity, but is absorbed in the body as time passes. Therefore, there is no need for abdominal surgery for removing the sponge after therapy.

CITATION LIST

Patent Literature

[PTL 1] JP 2005-287728 A
[PTL 2] JP 11-253564 A

Non Patent Literature

[NPL 1] The 21st Meeting of Japanese Society of Hepato-Biliary-Pancreatic Surgery (2009, Nagoya) MVS-8-11
[NPL 2] Journal of Japan Surgical Society Vol. 110 Supplement (2) p. 155 WS-1-4
[NPL 3] Biochem. Biophys. Res. Comm. 240: pp. 793-797 (1997)
[NPL 4] Nature Med. 4: pp. 321-327 (1998)
[NPL 5] Cancer Res. 53: pp. 5841-5844 (1993)

SUMMARY OF INVENTION

Technical Problem

Although the implant disclosed in Patent Literature 1 has a certain degree of viscosity, the implant is in a liquid state during and immediately after implantation, and hence when being implanted at a part under pressure between organs or the like, has a problem in that the implant does not reside in the implantation site and leaks into other parts owing to the influence of the pressure. This problem is particularly remarkable when the implant is implanted in a large amount at one time, and in the worst case scenario, the leaked implant prevents proper separation of a normal tissue being performed, resulting in a risk that sufficient therapy may not be performed. When the implant is implanted in small portions in order to avoid the problem, until a previously implanted portion of the implant increases in viscosity, a next portion of the implant cannot be implanted. As a result, a problem arises in that the process requires a large amount of time.

Further, as the sponge for radiation therapy disclosed in Patent Literature 2 is made spongy through lyophilization, growth of a cryohydrate for forming a porous part of the sponge is difficult to control, and hence uniform pore distribution cannot be attained through the entirety of the sponge. Accordingly, the sponge for radiation therapy includes a part with poor flexibility, and hence it is difficult to dispose the sponge for radiation therapy in close contact with an organ or the like without any void therebetween. A void part formed between the sponge for radiation therapy and the organ or the like may reduce in size owing to intraperitoneal pressure or the like as time passes. Hence, the resultant separation, being with a proper distance until immediately after the disposition of the spacer, becomes insufficient as time passes, resulting in a risk that a normal tissue may be exposed. Further, there is also a problem in that when the sponge for radiation therapy is compressed and used, the part with poor flexibility does not sufficiently recover to its original state in the body, and hence proper separation cannot be performed. In addition, collagen as a main material of the sponge is an animal-derived material produced mainly from cattle, swine, or the like, and hence involves a risk of infection with BSE or an endogenous retrovirus, which poses a safety problem as well.

In view of the foregoing, an object of the present invention is to provide such a spacer for ionizing radiation therapy that a lesion and an adjacent normal tissue can be separated reliably, the separated state undergoes little change, the spacer involves no risk of an infection such as BSE, and ionizing radiation irradiation of a normal tissue can be effectively blocked.

Solution to Problem

The inventors of the present invention have made extensive studies to achieve the object, and as a result, have found that the object can be achieved by a spacer including a fiber assembly obtained by three-dimensionally entangling a fibrous material formed of a biocompatible synthetic polymeric material. Thus, the present invention has been completed.

That is, the present invention includes the following.
1. A spacer for ionizing radiation therapy, including a fiber assembly obtained by three-dimensionally entangling a fibrous material formed of a biocompatible synthetic polymeric material.
2. A spacer for ionizing radiation therapy according to the above-mentioned item 1, in which the biocompatible synthetic polymeric material includes one of a bioabsorbable synthetic polymeric material and a non-bioabsorbable synthetic polymeric material.
3. A spacer for ionizing radiation therapy according to the above-mentioned item 1 or 2, in which the fiber assembly has a thickness of 1 mm to 100 mm.
4. A sheet for use in the production of the spacer for ionizing radiation therapy according to any one of the above-mentioned items 1 to 3, the sheet including a fiber assembly.

Advantageous Effects of Invention

The spacer for ionizing radiation therapy of the present invention has high flexibility and rebound resilience, and hence can be easily disposed between organs or the like in a close contact state with the organ or the like without any void therebetween and thus can separate a normal tissue from a lesion reliably. Further, an interfacial tension acts between each of the organs or the like and the spacer by virtue of water held in a surface of the spacer in a large amount, and hence the spacer attaches to the organs or the like and is not dislocated from the disposed position. Accordingly, the part in which the spacer has been disposed undergoes little positional change. In addition, the spacer of the present invention not only avoids exposure of a normal tissue by separation thereof from a lesion but also positively shields radiation by virtue of water stored in numerous voids formed in the fiber assembly. Thus, exposure of the normal tissue can be avoided more reliably than ever before, and as a result, radiation can be applied at an optimal dose for killing cancer cells without restricting the dose to be small, to thereby perform ionizing radiation therapy more effectively. When a bioabsorbable material is used for the biocompatible synthetic polymeric material, the material functions as a spacer during ionizing radiation therapy, and is absorbed in the living body after the completion of the therapy. Therefore, a burden on and a risk to a subject can be alleviated because of no need for removing the spacer through reopening of the abdomen after the completion of the ionizing radiation therapy. The spacer of the present invention can be used in therapy using a heavy particle beam or a proton beam as well as an X-ray or a γ-ray.

BRIEF DESCRIPTION OF DRAWINGS

FIG. 1 A perspective view illustrating an example of a spacer for radiation therapy according to the present invention (Example 1).

FIG. 2 An enlarged view illustrating a part of the structure of a fibrous material in the example illustrated in FIG. 1.

FIG. 3 An enlarged photograph showing a part of a surface in the example illustrated in FIG. 1.

DESCRIPTION OF EMBODIMENTS

A spacer for ionizing radiation therapy of the present invention includes a fiber assembly obtained by three-dimensionally entangling a fibrous material formed of a biocompatible synthetic polymeric material. The term "spacer for ionizing radiation therapy" as used herein comprehends not only a spacer having such a size and shape that the spacer may be actually used for a subject in ionizing radiation therapy but also one to be cut into an appropriate size and shape, i.e., a sheet for use in the production of a spacer for ionizing radiation therapy, the sheet including a fiber assembly. The size and shape of the spacer have only to have an appropriate thickness for providing water-containing property, and are not particularly limited. The thickness has only to allow water to be held, and may be set to, for example, 1 mm to 100 mm, preferably 2 mm to 20 mm, more preferably 5 mm to 15 mm.

The biocompatible synthetic polymeric material for constituting the spacer for ionizing radiation therapy of the present invention is a material that may be used for a medical device, has no toxicity to biological tissues and cells, and has no risk of an infection. Specifically, the material has only to be a polymeric material that does not cause any inflammatory reaction, immune reaction, or thrombogenic reaction in biological tissues and cells, and is produced through chemical synthesis not from an animal. As long as the material is as described above, the material may be a bioabsorbable synthetic polymeric material, or may be a non-bioabsorbable synthetic polymeric material. Of those, a bioabsorbable synthetic polymericmaterial is particularly suitably given.

The "bioabsorbable synthetic polymeric material" refers to a material that may be absorbed in a living body a predetermined time period after being left in the living body. Specific examples thereof include a poly(ester-ether), a poly(ester carbonate), a poly(acid anhydride), a polycarbonate, a poly(amide-ester), a polyacrylic acid ester, and an inorganic polymer. More specific examples thereof include at least one kind selected from poly(glycolic acid), poly(L-lactic acid), poly(DL-lactic acid), polyglactin (D/L=9/1), polydioxanone, glycolide/trimethylene carbonate (9/1), polycaprolactone, lactide (D, L, DL body), a glycolide-lactide (D, L, DL body) copolymer, a glycolide-ε-caprolactone copolymer, a lactide (D, L, DL body)-ε-caprolactone copolymer, poly(p-dioxanone), and glycolide-lactide (D, L, DL body)-ε-caprolactonelactide (D, L, DL body). In the case of a spacer formed of the bioabsorbable synthetic polymeric material, the spacer has only to reside in a desired site after being disposed during ionizing radiation therapy. Specifically, the spacer has only to reside for at least about 2 months after being disposed.

Examples of the non-bioabsorbable synthetic polymeric material include at least one kind selected from polyester, polyethylene, polypropylene, polybutester, polytetrafluoroethylene, polyamide, polyvinylidene fluoride, polyurethane, and vinylidene fluoride-hexafluoropropylene.

The spacer of the present invention includes a fiber assembly obtained by three-dimensionally entangling a fibrous material formed of the biocompatible synthetic polymeric material. The fiber assembly includes numerous voids communicating with each other substantially uniformly over its entirety because of fiber pieces three-dimensionally entangled with each other, and is capable of storing a large amount of water in the voids through utilization of capillarity or the like. Further, the fiber assembly has high flexibility while having high rebound resilience because of the three-dimensionally entangled fibrous material. As such fiber assembly, any one of a three-dimensional woven fabric, a three-dimensional knitted fabric, and a nonwoven fabric may be adopted. Of those, a nonwoven fabric is particularly suitable because a bulky product may be produced from a small amount of a fibrous material, and there is easily produced a fiber structure providing substantially uniform distribution of voids in a spacer and having high flexibility, rebound resilience, and water-containing property at an arbitrary thickness and density. For example, when the woven fabric or the knitted fabric is adopted, the woven fabric or the knitted fabric may be produced using, as a fibrous material, a thread processed into any one of a monofilament thread, a multi-filament thread, a twisted thread, a braided thread, and the like, preferably a monofilament thread. The woven fabric or the knitted fabric may be produced by a method known per se. In the case of the nonwoven fabric, there may be used, for the fibrous material, a fiber or monofilament thread formed of the bioabsorbable synthetic polymeric material or non-bioabsorbable synthetic polymeric material described above, or a multi-filament thread, a twisted thread, or a braided thread prepared from the fiber or monofilament. The nonwoven fabric may also be produced by a method known per se. Specifically, the nonwoven fabric may be produced by a production method such as a needle punching method, a chemical bonding method, a thermal bonding method, or a spun lace method. It should be noted that as a fiber to be used for the fibrous material, there may be used not only a fiber having a circular cross-section, but also a fiber having a modified cross-section of, for example, a chrysanthemum flower, star, or cross shape, which includes grooves on a fiber surface, or a hollow fiber. In the latter cases, capillarity is more strongly exhibited than in the case of using the fiber having a circular cross-section, and hence a fiber assembly having a high water-absorbing ability may be produced. Further, the crimp of the fibrous material is not particularly limited, but a fibrous material having a crimp is suitable because a fiber assembly being bulky and excellent in rebound resilience can be produced with only a small amount of the fibrous material.

The disposition of the spacer of the present invention between a lesion (part to be irradiated with radiation) and a normal tissue adjacent to the lesion allows the normal tissue to be separated to a position with no risk of exposure. In addition, when the spacer contains water, radiation can be shielded and a normal tissue can be effectively protected from exposure by virtue of the water. The spacer of the present invention stores water in voids in the fiber assembly through utilization of capillarity by the fibrous material or the like and thus contains water. From the viewpoint that radiation is shielded by virtue of water, a ratio at which the spacer contains water is preferably adjusted to, in terms of water content by weight, at least 90% or more, preferably 95% or more, more preferably 99% or more. In this case, the water content by weight (A) may be expressed by the following equation with the weight of water (W) and the weight of a dried product of the spacer for radiation therapy of the present invention (V).

$$A=[W/(W+V)]\times 100$$

It should be noted that the spacer of the present invention does not need to be in a water-containing state from before its use, and has only to be in a water-containing state during ionizing radiation therapy. As long as the spacer is in a water-containing state during the therapy, when the spacer is left in a living body, the spacer may be caused to contain water in advance and disposed, or the spacer in a dry state may be disposed and caused to absorb water in the living body. In the case where the spacer is caused to contain water in advance, the water has only to be a liquid that may be used in a living body, and is not particularly limited. In particular, an isotonic solution is preferred, and more specifically, a physiological saline solution may be used. In the case where the spacer in a dry state is disposed, the spacer has only to be caused to contain water by water in the living body, such as ascitic fluid during a time period from when the spacer is disposed in a desired site through surgery or the like until ionizing radiation therapy is performed. In ordinary cases, ionizing radiation therapy is performed about 2 weeks to 2 months after the spacer has been disposed in a living body through surgery, and hence the spacer falls in a water-containing state by water in the living body by the start of the therapy. When the spacer is in a water-containing state, an interfacial tension acts between the spacer and an organ or the like, and hence the spacer attaches to the organ or the like and is not dislocated from the disposed position. Accordingly, the part in which the spacer is disposed undergoes little positional change.

The spacer or sheet of the present invention may be cut into a desired size and shape as required before being disposed in a living body. The size and shape of a spacer to be used in ionizing radiation therapy are set in consideration of various factors such as the age, body weight, and sex of a subject, a site in which the ionizing radiation therapy is performed, the size and shape of an object to be irradiated, a distance to be separated, a tissue to be separated, and the residence time of the spacer. Further, the thickness of the spacer may also be appropriately determined in consideration of various factors as in the foregoing. For example, a plurality of spacers may be laminated and used as required. The thickness of the plurality of spacers after the lamination is not particularly limited and may be, for example, 100 mm or more.

The spacer of the present invention is used as an aid for ionizing radiation therapy, preventing exposure of any other tissue than a tissue to be treated in the ionizing radiation therapy. In view of this, a site in which the spacer is disposed has only to be a site according to a therapeutic purpose, and is not particularly limited.

In the present invention, the ionizing radiation therapy may be performed for not only malignant tumors but also some benign diseases, for example, in improving a keloid and treating thyroid ophthalmopathy. When the ionizing radiation therapy is performed for a malignant tumor, the tumor has only to be a solid cancer, and is not particularly limited. Examples thereof may include a head and neck tumor, a skull base tumor, anon-small-cell lung cancer, a mediastinal tumor, a hepatocellular cancer, a pancreatic cancer, a stomach cancer, a prostate cancer, a rectal cancer, a vaginal cancer, a metastatic tumor (solitary), and a bone and soft tissue tumor. The spacer of the present invention may be used for ionizing radiation therapy on any of the malignant tumors listed above. In particular, the spacer of the present invention is useful for a tissue or organ not to be treated which is vital to the sustenance of a living body, such as heart or a digestive organ such as stomach, large intestine, or small intestine because the use of the spacer of the present invention in ionizing radiation therapy on a tumor or the like appearing in the vicinity of the tissue or organ may alleviate an adverse effect of the ionizing radiation therapy.

The kind of radiation in ionizing radiation therapy for which the spacer of the present invention may be used may be appropriately selected depending on a therapeutic purpose and other conditions. For example, there may be adopted any of a proton beam and a heavy particle beam as well as an X-ray and a γ-ray.

The spacer of the present invention may be provided with an appropriate marker. The position and shape of the spacer, for example, may be easily monitored in a living body by means of X-ray illumination, X-ray CT, MRI, an ultrasonic echo, a radioisotope image, or the like. A substance that may serve as the marker is, for example, a metal or a contrast medium, and examples of the contrast medium include an iodine contrast medium and a barium-containing contrast medium.

Considering that the spacer of the present invention is disposed in a living body, the spacer is preferably produced in a sterile room or sterilized after being produced. As a sterilization method, a sterilization method known per se such as autoclave sterilization, EOG sterilization, γ-ray sterilization, electron beam sterilization, or a plasma sterilization method may be applied. Alternatively, a sterilization method to be developed in the future may be applied.

EXAMPLES

For further understanding of the present invention, the present invention is hereinafter specifically described by way of examples. However, the present invention is by no means limited to the following examples.

(Example 1) Spacer for Ionizing Radiation Therapy

FIG. 1 is a perspective view illustrating the spacer for ionizing radiation therapy according to the present invention. In Example 1, a synthetic absorbable suture Ope-Polyx™ (manufactured by Alfresa Pharma Corporation) was used as the fibrous material formed of a biocompatible synthetic polymeric material. The suture is a multi-filament thread produced by twisting together three fiber pieces drawn from a pellet. The thread is not subjected to any crimp processing and is a straight-type thread. The thread is formed of polyglycolic acid, and hence, when left in a living body, is hydrolyzed to have its tensile strength reduced by half in about 3 weeks, and to be absorbed in the living body in about 3 months with no thread form left. Thus, the thread has bioabsorbability-type biocompatibility. In order to produce a spacer for ionizing radiation therapy of Example 1, a large number of threads each having a length of about 50 mm and cut out from the above-mentioned thread were prepared, and a fibrous web was produced from these threads with a carding apparatus. The produced web was subjected to needle punch processing, so that the threads were three-dimensionally entangled as illustrated in FIG. 2, to produce a nonwoven fabric having a weight per unit area of 0.0716 g/cm$^2$, an apparent density of 0.0716 g/cm$^3$, and a thickness of 10 mm. Then, the nonwoven fabric was cut into a rectangular shape measuring 15 cm square and the resultant was defined as Example 1. Hereinafter, the spacer produced in this example is referred to as "nonwoven fabric spacer." As shown in FIG. 3, the nonwoven fabric spacer of this example is formed in a state in which numerous fine voids communicate with each other, and is formed in a state in which voids are exposed in the surface. Thus, the nonwoven fabric spacer of this example absorbs and holds physiological saline, an intraperitoneal fluid, or the like immediately upon contact therewith through a capillary action.

(Comparative Example 1) GORE-TEX™ Spacer

A Soft Tissue Patch (product No. 13150S: 150 mm×200 mm×2.0 mm) commercially available as a tissue-reinforcing material was used as a comparative example.

(Experimental Example 1) Test on Water-Containing Property of Spacer for Ionizing Radiation Therapy In order to measure the water-containing property of each of the nonwoven fabric spacer produced in Example 1 and the GORE-TEX™ spacer of Comparative Example 1, a test was performed by the following procedure.

Test Method:
1. Example 1 and Comparative Example 1 were each cut into a rectangular shape measuring 5 cm square to serve as a test sample, which was left to stand still on a petri dish.
2. Water was gradually dropped with a dropper on an edge of the test sample, and the amount of water dropped when water exuded from the bottom of the petri dish was quantified, which was defined as a water retention amount.

Table 1 shows the results.

TABLE 1

| Item | | Comparative Example 1 | Example 1 |
|---|---|---|---|
| Physical properties of test sample | Thickness (mm) | 2 | 10 |
| | Weight per unit area (g/cm$^2$) | 0.1368 | 0.0716 |
| | Weight (g) | 3.42 | 1.79 |
| | Apparent density (g/cm$^2$) | 0.6840 | 0.0716 |
| Water retention amount (g) | | 0.25 | 23.61 |
| Water retention rate (g/cm$^2$) | | 0.0100 | 0.9444 |
| Water retention rate (g/cm$^3$) | | 0.0500 | 0.9444 |
| Water content by weight (%) | | 6.81 | 92.95 |

As shown in Table 1, the test samples have different thicknesses, and hence comparison of their water-containing properties is performed in terms of water content by weight. It has been confirmed that Example has as very high water-containing property as a water content by weight of 92.95% as compared to the water content by weight of Comparative Example, i.e. 6.81%.

(Experimental Example 2) Radiation Blocking Test on Spacer for Ionizing Radiation Therapy 1) Measurement of Water Equivalent Thickness of Spacer Each of a laminate of two pieces of the spacer of the present invention produced in Example 1 and a laminate of two pieces of the GORE-TEX™ spacer as Comparative Example 1 (thickness: 4 mm) was subjected to CT scanning in the same manner as in general particle beam therapy. Then, a water equivalent thickness determined with a therapy planning apparatus (instrument measurement value) and a water equivalent thickness determined through actual measurement using a particle beam (actual measurement value) were compared to each other. The term "water equivalent thickness" as used herein refers to the shield ability of a shield converted in terms of water thickness (equal to the thickness of an aqueous medium contained in the shield), which serves as an indicator for the radiation stopping power of the shield. Table 2 shows the results. The spacer of the present invention is a sheet formed by three-dimensionally entangling threads, and its water equivalent thickness had a value substantially similar to that of air. The results suggest that, in a dry state, the spacer of the present invention cannot stop a particle beam.

TABLE 2

| | A (mm) | B (mm) |
|---|---|---|
| Comparative Example 1 | 1.3 (0.325)* | 1.5 (0.375)* |
| Example 1 | 0.3 (0.015)* | 1.2 (0.06)* |

A: Instrument measurement value obtained with therapy planning apparatus
B: Actual measurement value obtained using particle beam
*Value per unit thickness 2) Radiation Blocking Test on Spacer of Example 1 after Water Absorption In this test, a water equivalent thickness was measured for the spacer of the present invention produced in Example 1 in each of a dry state and a water-absorbed state. Table 3 shows the results. In the dry state, the water equivalent thickness was 0.5 mm, while the water equivalent thickness became 11.6 mm after water absorption, being about 23 times that in the dry state. Further, a water equivalent thickness per unit thickness was calculated to be 0.05 mm in the dry state, and 1.16 mm after water absorption. The results show that the spacer of the present invention produced in Example 1 exerts high shielding performance through water absorption. It should be noted that the fact that the water equivalent thickness of the spacer in the water-absorbed state was larger than the thickness of the spacer in the dry state is probably due to the expansion of the spacer through water absorption by virtue of a high water-absorbing ability.

TABLE 3

| | Dry state (mm) | After water absorption (mm) |
|---|---|---|
| Example 1 | 0.5 (0.05)* | 11.6 (1.16)* |

*Value per unit thickness

The invention claimed is:

1. A method of avoiding exposure of a non-target tissue adjacent a target tissue subject to ionizing radiation therapy comprising:
   placing a spacer between the target tissue and the non-target tissue, the spacer comprising a fiber assembly obtained by three-dimensionally entangling a fibrous material formed of a biocompatible synthetic polymeric material, wherein the fiber assembly includes voids;
   absorbing an aqueous liquid by the spacer prior to or after said placing of the spacer between the target tissue and the non-target tissue, wherein the spacer with the absorbed aqueous liquid has an aqueous liquid content of at least 90 wt. % based on the combined dry weight of the spacer and the weight of the aqueous liquid contained by the spacer; and
   performing ionizing radiation therapy on the target tissue with the spacer storing absorbed aqueous liquid present.

2. The method of claim 1, wherein the biocompatible synthetic polymeric material consists of a bioabsorbable synthetic polymeric material.

3. The method of claim 2, wherein the bioabsorbable synthetic polymeric material consists of any one or more selected from a poly(ester-ether), a poly(ester carbonate), a poly(acid anhydride), a polycarbonate, a poly(amide-ester), a polyacrylic acid ester, and an inorganic polymer.

4. The method of claim 2, wherein the bioabsorbable synthetic polymeric material consists of any one or more selected from poly(glycolic acid), poly(L-lactic acid), poly(DL-lactic acid), polyglactin (D/L=9/1), polydioxanone, glycolide/trimethylene carbonate (9/1), polycaprolactone, lactide (D, L, DL body), a glycolide-lactide (D, L, DL body) copolymer, a glycolide-ε-caprolactone copolymer, a lactide (D, L, DL body)-ε-caprolactone copolymer, poly(p-dioxanone), and glycolide-lactide (D, L, DL body)-ε-caprolactonelactide (D, L, DL body).

5. The method of claim 1, wherein the fiber assembly has a thickness of 1 mm to 100 mm.

6. The method of claim 1, further comprising producing the spacer from a sheet consisting of the fiber assembly.

7. The method of claim 1, wherein the fiber assembly consists of a three-dimensional woven fabric, a three-dimensional knitted fabric, or a nonwoven fabric.

8. The method of claim 1, wherein said spacer absorbs the aqueous liquid by allowing the fiber assembly to absorb the aqueous liquid in a patient's body after the placing of the spacer between the target tissue and the non-target tissue and before the performing of the ionizing radiation therapy.

9. The method of claim 8, wherein the ionizing radiation therapy is performed 2 weeks to 2 months after the placing of the spacer between the target tissue and the non-target tissue.

10. The method of claim 1, wherein said spacer absorbs the aqueous liquid by absorbing the aqueous liquid into the fiber assembly prior to placing of the spacer between the target tissue and the non-target tissue.

11. The method of claim 1, wherein the ionizing radiation therapy is performed 2 weeks to 2 months after the placing of the spacer between the target tissue and the non-target tissue.

* * * * *